US00PP26418P3

(12) United States Plant Patent
Costin et al.

(10) Patent No.: US PP26,418 P3
(45) Date of Patent: Feb. 16, 2016

(54) ***LOMANDRA HYSTRIX* PLANT NAMED 'LMV200'**

(50) Latin Name: *Lomandra hystrix*
Varietal Denomination: LMV200

(71) Applicants: Russell Costin, Limpinwood (AU); Sharon Costin, Limpinwood (AU)

(72) Inventors: Russell Costin, Limpinwood (AU); Sharon Costin, Limpinwood (AU)

( * ) Notice: Subject to any disclaimer, the term of this patent is extended or adjusted under 35 U.S.C. 154(b) by 93 days.

(21) Appl. No.: 13/999,838

(22) Filed: Mar. 27, 2014

(65) Prior Publication Data
US 2015/0282415 P1 Oct. 1, 2015

(51) Int. Cl.
*A01H 5/12* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Samuel R. McCoy, Jr.

(57) ABSTRACT

'LMV200' is a distinctive variety of *Lomandra hystrix* which is characterized by the combination of an arched foliage habit and the presence of light yellow to green leaf variegation.

3 Drawing Sheets

Latin name of the genus and species: The Latin name of the genus and species of the novel variety disclosed herein is *Lomandra hystrix.*

Variety denomination: The inventive variety of *Lomandra hystrix* disclosed herein has been given the variety denomination 'LMV200'.

BACKGROUND OF THE INVENTION

The present invention relates to a new and distinct perennial variety of *Lomandra hystrix,* which has been given the variety denomination of 'LMV200'. Its market class is that of an ornamental plant. 'LMV200' is intended for use in landscaping and as a decorative plant.

Parentage: In March 2005, seed from openly-pollinated *Lomandra hystrix* was sown at a commercial nursery operation in Limpinwood, NSW Australia. The resulting seedlings were potted and grown on as nursery stock. In November 2005 the variety now called 'LMV200' was selected from said seedlings for exhibiting leaf variegation whereas the parent plant and all other resulting progeny did not.

Asexual Reproduction: 'LMV200' was first propagated asexually by division in Limpinwood, NSW Australia and has since been propagated through 7 subsequent generations. The distinctive characteristics of the inventive 'LMV200' variety have proven to be stable from generation to generation; clones of the variety produced by asexual reproduction maintain the distinguishing characteristics of the original plant.

SUMMARY OF THE INVENTION

'LMV200' is a distinctive variety of *Lomandra hystrix* which is characterized by the combination of an arched foliage habit and the presence of light yellow to green leaf variegation.

BOTANICAL DESCRIPTION OF THE PLANT

Figure 1:
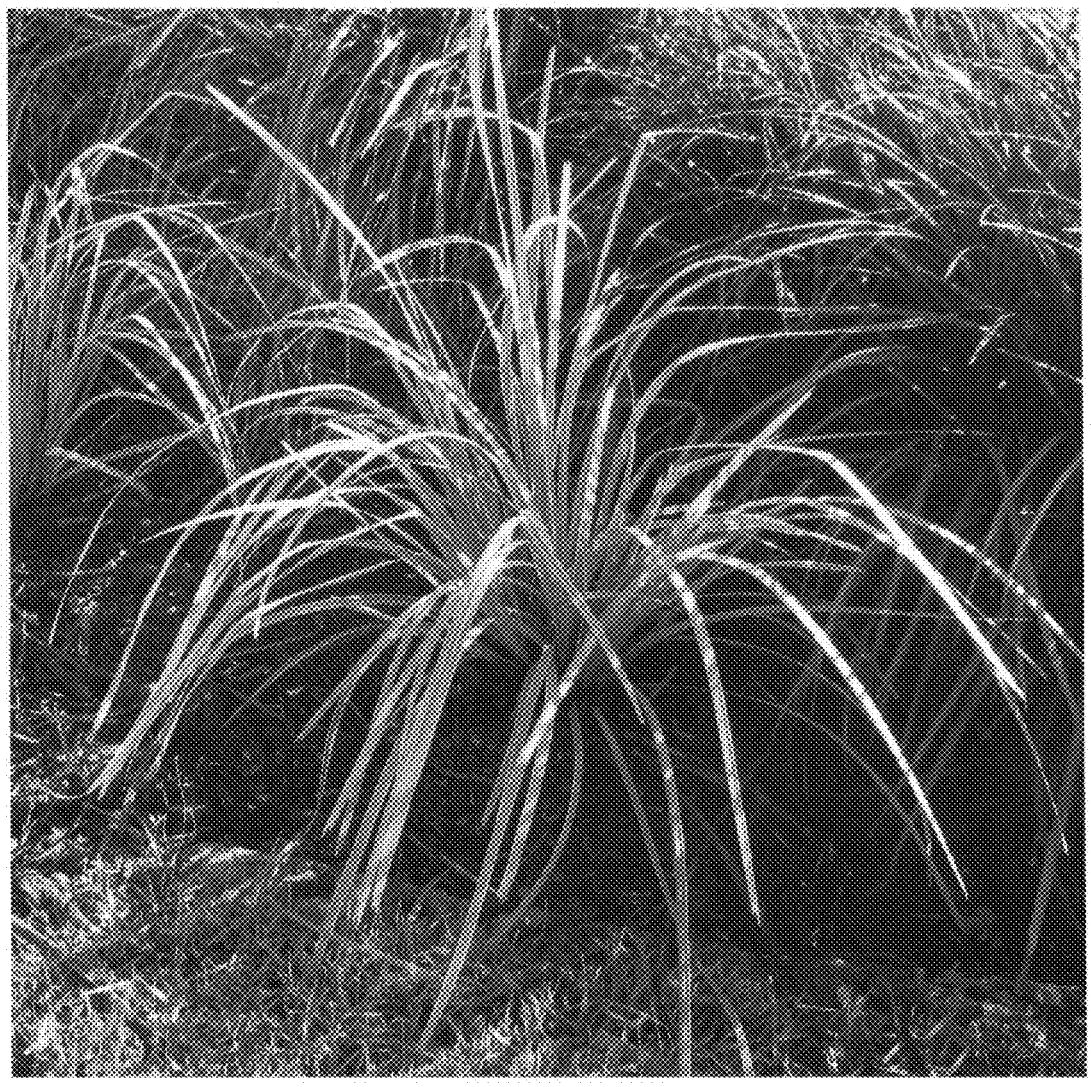
FIG. 1 illustrates an exemplary mature 'LMV200' plant of 12 months of age.
Figure 2:
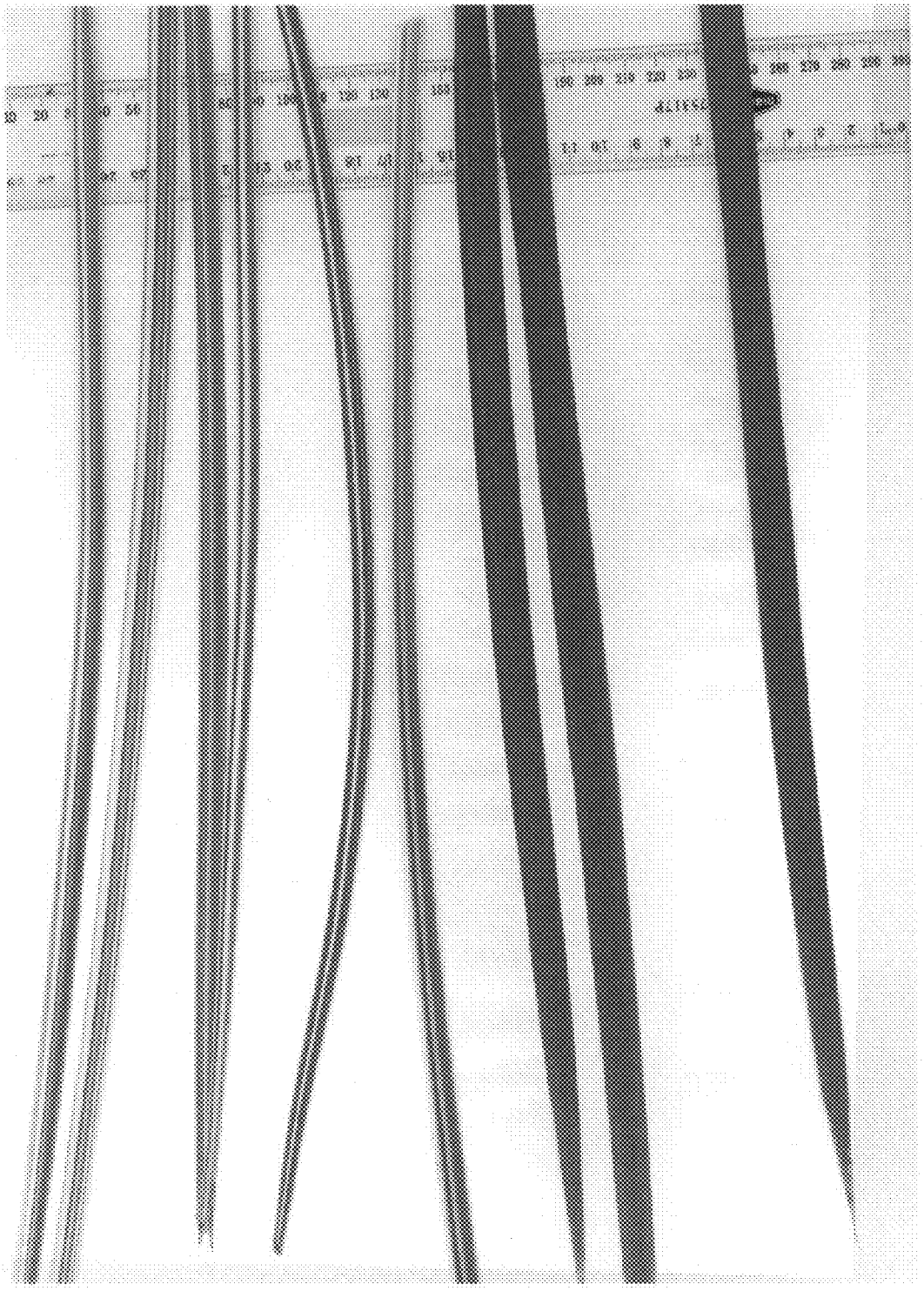
FIG. 2 illustrates the typical variegation pattern of 'LMV200' (left) by comparison with the parent (right).

The following is a detailed botanical description of a new and distinct variety of a *Lomandra hystrix* ornamental plant known as 'LMV200'. Plant observations were made on plants grown in Limpinwood NSW, Australia. Unless indicated otherwise, the descriptions disclosed herein are based upon observations made of 18 month old 'LMV200' plants grown outdoors from rooted cuttings from November 2010 to August 2011 in 400 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'LMV200' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1986 edition. Note that generic color descriptions such as 'white' do not exist in the R.H.S. charts and the corresponding R.H.S. colors are quoted.

'LMV200' is a variegated form of *Lomandra hystrix* plant which is a seedling selection from a *Lomandra hystrix* (common form). These features and other characteristics are apparent from the description provided below.

Growth Habit, Dimensions and Color

Plant description:

*Propagation.*—Propagation is accomplished by dividing the crown of the plant. Time to develop roots is approximately 3 to 4 weeks and an average crop time is approximately 9 months to produce a mature and marketable 3-gallon nursery container, starting from a rooted cutting.

*Plant habit*.—Grass-like perennial with arched foliage; rhizomatous plant forming a dense tussock.

*Reproduction*.—Dioecious; male of the species.

*Height*.—90 cm as measured.

*Width*.—100 cm as measured.

*Bloom period*.—Spring.

*Hardiness*.—USDA Zone 9 to 11.

*Environmental tolerances*.—Shade and drought tolerant.

*Pest and disease susceptibility or resistance*.—In common with the species, none of note.

Roots: Similar to other *Lomandra hystrix,* 'LMV200' has a large root structure; roots are fibrous and spreading.

Rhizomes: Short (3 cm to 4 cm); rhizome color with the leaf sheath removed is white (RHS 155C); surface texture of the rhizome is smooth.

Foliage:

*Type*.—Evergreen.

*Shape*.—Linear; grass-like.

*Division*.—Simple.

*Arrangement*.—Whorled around an indistinguishable culm.

*Apex*.—Tridentate. The leaf apex may become locally necrotic in response to moisture stress.

*Base*.—Sheathed attachment to the culm.

*Margins*.—Entire; margins may shred at the base. The basal leaf margin color prior to any shredding consists of brown RHS 200D.

*Mature leaf dimensions*.—The leaf blade is generally 13 to 16 mm in width and 70-90 cm in length average length 12.5 mm, average width 2.5 mm. The leaf is generally a uniform width, narrowing only slightly from base to apex.

*Leaf color, juvenile*.—Parallel variegation; both the adaxial and abaxial surfaces comprised of a combination of light yellow (RHS 4D) to green (approximating to RHS 143A to 143B), with the majority of the leaf surface appearing to be comprised of green (approximating to RHS 143A to 143B).

*Leaf color, mature*.—Parallel variegation; both the adaxial and abaxial surfaces comprised of a combination of light yellow (RHS 4D) to green (approximating to RHS 143A to 143B), with the majority of the leaf surface appearing to be comprised of yellow (RHS 4D).

*Venation*.—Parallel.

*Vein color* (*adaxial surfaces*).—Indistinguishable from surrounding foliage.

*Vein color* (*abaxial surfaces*).—Indistinguishable from surrounding foliage.

*Surface texture* (*adaxial surface*).—Glabrous; smooth with light glaucosity.

*Surfaces texture* (*abaxial surface*).—Glabrous; smooth.

Figure 3:
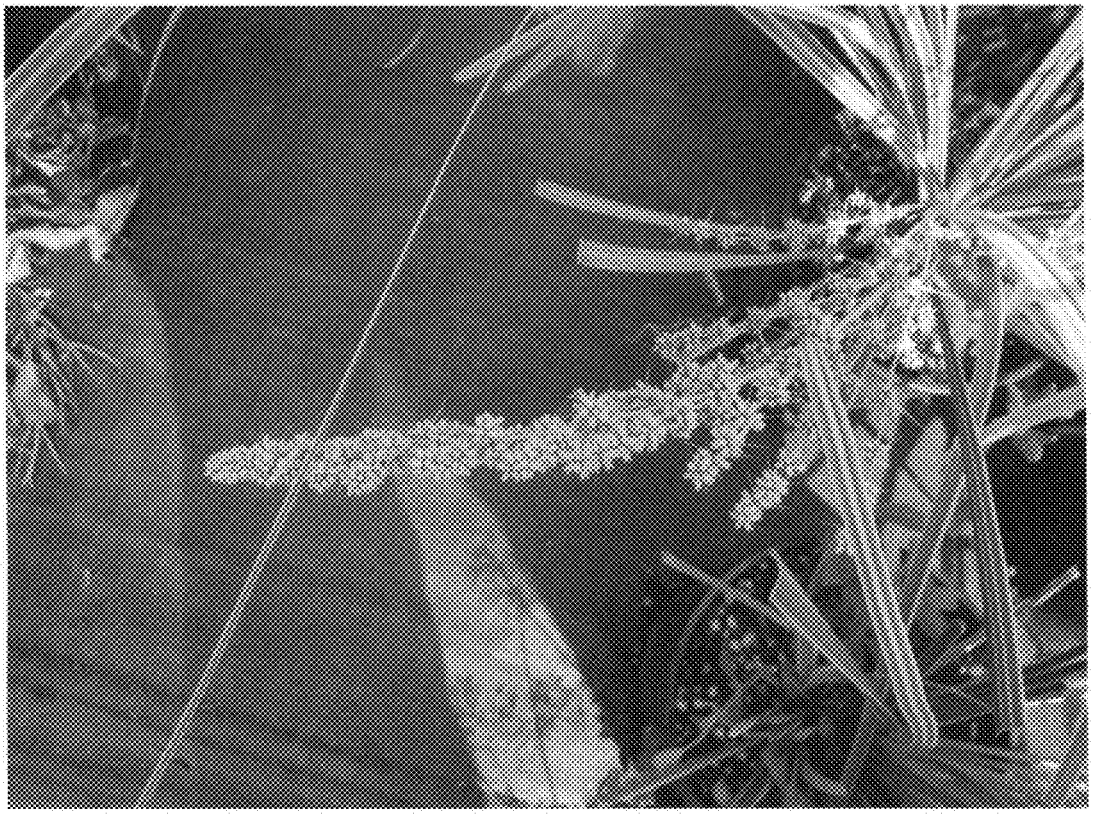
FIG. 3 illustrates the flower of a 'LMV200' plant.

Inflorescence: The inflorescence is a panicle with single branching and usually 4 branches per node; branch angles are acute. Flowers are male and borne in whorled clusters around each node. Each cluster of flowers is subtended by 4 bracts of length 8 to 16 mm. Inflorescence height is from 20 to 30 cm and inflorescence width is from 4 to 7 cm. The peduncle is approximately 70 cm long and 3 to 5 mm in diameter, flattened in profile, and peduncle color is approximately yellow-green (RHS 144C to 144D). Panicles are persistent, flowering for approximately 3 weeks and remaining for approximately an additional 6 weeks after flowering. FIG. 3 shows an exemplary inflorescence of 'LMV200'.

Flowers: Flowers are male and borne in clusters around inflorescence nodes. Tepal color is a dull yellow corresponding approximately to RHS 10A to 10B. Flower length is 3 to 4 mm usually.

Flower rachis: The length of the flower rachis (the branch of the panicle) varies from approximately 23 mm to 38 mm long, with longer rachis near the base of the panicle, and appears to exhibit indeterminate growth.

Reproductive organs of male florets: Six stamens, anther size is less than 1 mm in length, anther color is yellow (approximately RHS 8B).

Seed: Flowers are male; seed is not produced.

Comparison of 'LMV200' with Other Varieties of *Lomandra hystrix*

The only variegated form of *Lomandra hystrix* known to the breeder is *Lomandra hystrix* 'WN02'. While 'LMV200' is similar to 'WN02' in certain ways, there are certain distinct characteristics exhibited by 'LMV200'.

The culm attitude and, subsequently, the leaf attitude of 'LMV200' is described as being erect whereas the culm and leaf attitude of 'WN02' is described as spreading; "spreading" being defined as having an attitude that is more horizontally oriented than vertically oriented. This results in 'LMV200' exhibiting an arched form as opposed to 'WN02' which exhibits a mounded form. For the purposes of this specification, "arched" is defined as a grassy perennial having foliage that grows upward and then outward in somewhat equal portions and "mounded" is defined as a grassy perennial with somewhat weeping and mounding foliage.

While both 'LMV200' and 'WN02' could be described as possessing cream and green foliage variegation, the actual shades of cream and green colors appear significantly different between the two varieties. With respect to the cream portion of the foliage variegation, 'LMV200' exhibits a lighter shade of yellow that is more closely associated with the green-yellow RHS Color Group, corresponding to RHS 4D (both in mature and immature foliage and on the adaxial and abaxial surfaces), whereas 'WN02' exhibits a darker shade of yellow corresponding to RHS 13C which is closely associated with the yellow-orange RHS Color Group. With respect to the green portion of the foliage variegation, the foliage of 'LMV200' is green (RHS 143A to 143B) on both the mature and immature foliage and on the adaxial and abaxial surfaces whereas 'WN02' is yellow-green (RHS 146A).

This combination of an arched form and light yellow and green variegated foliage distinguished 'LMV200' from the comparator and makes it a desirable ornamental plant suited for mass production for pot and landscape use.

That which is claimed is:

1. A new and distinct variety of *Lomandra hystrix* plant named 'LMV200', substantially as described and illustrated herein.

* * * * *